United States Patent
Mullani

(10) Patent No.: US 10,206,578 B1
(45) Date of Patent: Feb. 19, 2019

(54) COMBINATION ARTERIAL AND VEIN TRANSILLUMINATION DEVICE USING YELLOW-ORANGE, LIME GREEN AND AMBER LED LIGHTS

(71) Applicant: Nizar Mullani, Sugar Land, TX (US)

(72) Inventor: Nizar Mullani, Sugar Land, TX (US)

( * ) Notice: Subject to any disclaimer, the term of this patent is extended or adjusted under 35 U.S.C. 154(b) by 0 days.

(21) Appl. No.: 15/801,429

(22) Filed: Nov. 2, 2017

(51) Int. Cl.
| | |
|---|---|
| A61B 5/00 | (2006.01) |
| A61B 90/30 | (2016.01) |
| F21Y 115/10 | (2016.01) |
| F21Y 113/10 | (2016.01) |
| F21Y 113/13 | (2016.01) |

(52) U.S. Cl.
CPC .......... *A61B 5/0064* (2013.01); *A61B 5/0059* (2013.01); *A61B 90/30* (2016.02); *F21Y 2113/10* (2016.08); *F21Y 2113/13* (2016.08); *F21Y 2115/10* (2016.08)

(58) Field of Classification Search
CPC . A61B 5/0064; A61B 5/0059; F21Y 2103/10; F21Y 2115/10; F21Y 2113/13
See application file for complete search history.

(56) References Cited

U.S. PATENT DOCUMENTS

| | | | |
|---|---|---|---|
| 6,230,046 B1 | 5/2001 | Crane et al. | |
| 7,874,698 B2 * | 1/2011 | Mullani | A61B 5/0059 362/230 |
| 8,789,962 B2 * | 7/2014 | Crowder | A61B 90/35 362/105 |
| 2004/0218387 A1 * | 11/2004 | Gerlach | F21K 9/00 362/231 |
| 2005/0026125 A1 | 2/2005 | Toly | |
| 2007/0244371 A1 | 10/2007 | Nguyen et al. | |
| 2009/0103296 A1 | 4/2009 | Harbers et al. | |
| 2015/0342495 A1 | 12/2015 | Davis et al. | |
| 2016/0242649 A1 * | 8/2016 | Mullani | A61B 5/0077 |

* cited by examiner

*Primary Examiner* — Robert J May
(74) *Attorney, Agent, or Firm* — Welsh, Flaxman & Gitler LLC

(57) ABSTRACT

A transillumination device having a yellow-orange light source, with LEDs having a wavelength in the range of 585-595 nm, preferably 590 nm, an amber light source with LEDs having a wavelength of light in the range of approximately 600-610 nm, preferably 605 nm, and a lime green LEDs light source having a wavelength in the range of approximately 535-545 nm, preferably 540 nm. Yellow-orange LED light sources have been found to be beneficial for transillumination of superficial veins, amber light sources have been found to be beneficial for transillumination of deeper veins and lime green light sources have been found to be beneficial for transillumination of arteries.

2 Claims, 5 Drawing Sheets

COMBINATION ARTERIAL AND VEIN TRANSILLUMINATION DEVICE USING YELLOW-ORANGE, LIME GREEN AND AMBER LED LIGHTS

BACKGROUND OF THE INVENTION

1. Field of the Invention

The invention relates to a transillumination device. More particularly, the invention relates to a transillumination device with a yellow-orange light source, an amber light source and a lime green light source.

2. Description of the Related Art

Transillumination entails shining of a light through a body cavity or organ for diagnostic purposes. Typically, transillumination is performed in a room where the lights have been dimmed or turned off to facilitate the viewing of the part being studied. A bright light is pointed at the cavity or organ and, due to the slight translucence of the part under consideration, some of the light passes through the part or organ. This test is often performed on newborns or infants with hydrocephalus or males suspected of having hydrocele. In addition, transillumination is used for tests performed on breast tissue to detect lesions and/or cysts. In newborns, the test is used to transilluminate the chest cavity if pneumothorax is suspected. Only in newborns is transillumination of the chest possible. Transillumination is painless and quickly performed with inexpensive equipment. It is often the only method of finding veins in prematurely born babies. (neonates)

Transilluminators use color to facilitate the viewing of the tissue organ under study. U.S. Pat. No. 4,651,743 issued to Stoller discloses a transillumination device using red light. In addition, U.S. Pat. No. 5,957,917 issued to Doiron et al. discloses that red light is particularly useful for performing transillumination of tissue for diagnostic purposes. Further, U.S. Pat. No. 7,874,698 issued to Mullani relates to transillumination having an orange color light. These devices use colored light at a specified wavelength to illuminate veins that are positioned below a skin surface. Typically, the vein transilluminator uses a side-transillumination method where light shines into the skin from the top and at an angle to the skin so that the light is focused approximately 2 cm to 4 cm below the skin. The annulus of focused light behaves like a virtual light source under the skin and transilluminates an area of the skin inside the circle of light. Further still, green light is known to be used for examination of arteries below the skin.

With this in mind, multiple devices must be used for the evaluation of various bodily structures. For example, and when it is the desire for the user to examine the arteries below the skin of a patient, a separate device that uses green LED lights of a particular wavelength is utilized. In order to do an exam of veins below the skin of a patient, a separate yellow-orange LED light source of a particular wavelength is used, and when one wishes to do an examination of veins that are deeper below the surface of the skin of a patient, a separate amber LED light source of a particular wavelength is used. As a result three separate devices are required for complete transillumination; one for transillumination the arteries, one for examination of veins that are not too deep below the surface of the skin, and a third for examination of veins that have a deeper location.

SUMMARY OF THE INVENTION

A transillumination device comprises, in combination, a housing having a first end, a second end, a top surface, and a bottom surface. A yellow-orange first light source, an amber second light source, and a lime green third light source are located at the first end of the housing along the top surface of the housing. The first LED light source is composed of LEDs producing light having a wavelength in the range of from 585-595 nm for illumination of shallow veins, the second LED light source is composed of LEDs producing light having a wavelength in the range of 600-610 nm for transillumination of deeper veins, and the third LED light source is composed of LEDs producing light having a wavelength in the range of 535-545 nm for illumination of arteries. The device further includes an on/off switch for turning the transillumination device on and off and a light control switch located on the bottom portion of the cylindrical housing for controlling the light generating source. Also provided is a power source contained within a power compartment with an opening at the bottom surface of the transillumination device.

It is also an object of the invention to provide a unique portable, battery powered transillumination device that combines three separate and distinct functions, namely, transillumination of shallow veins, transillumination of deep veins and artery examination via transillumination. Therefore, different functions employ separate and distinct light sources, thus eliminating the need to have three separate transillumination devices with three different light sources.

It is another object of the invention to provide a simplified transillumination device that can easily switch between three LED light sources, or a combination of two colors or all three colors simultaneously to create a very bright light source for pneumothorax examination in neonates.

It is another object of the invention to have a transillumination device with three unique types of LED light sources for transillumination of superficial veins, deeper veins and arteries via a unique portable battery operated device.

These and other objects of the invention will become apparent to one of ordinary skill in the art after reviewing the disclosure of the invention.

DETAILED DESCRIPTION OF THE INVENTION

Figure 1:
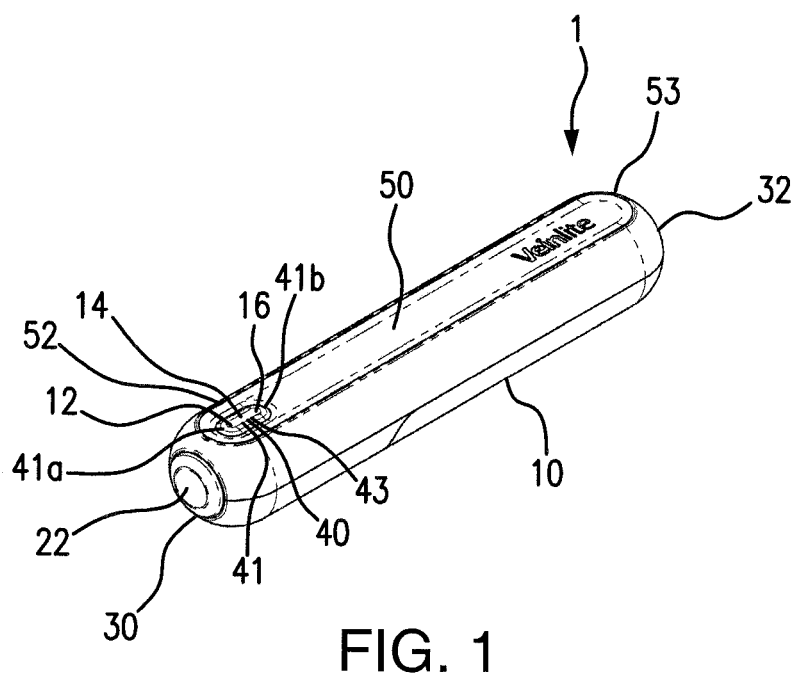
FIG. 1 is a rear angled perspective top view of the transillumination device.
Figure 2:
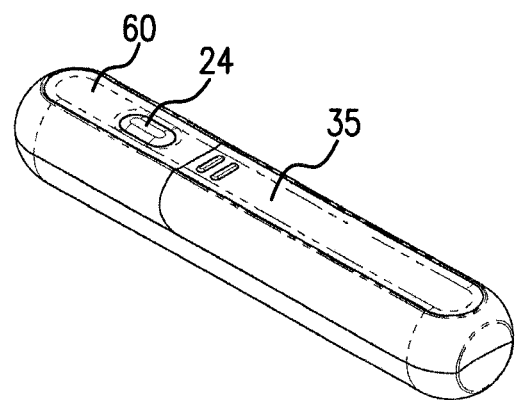
FIG. 2 is a front angled perspective top view of the transillumination device.
Figure 3:
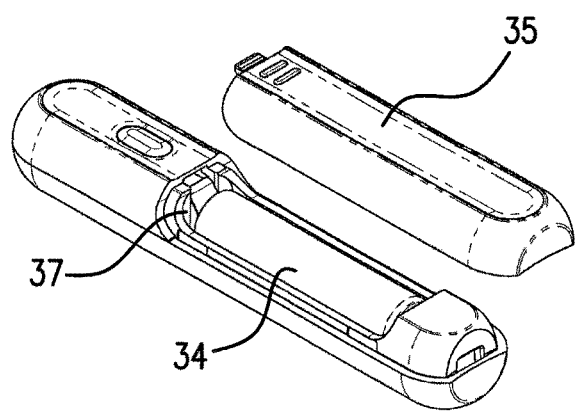
FIG. 3 is an exploded front angled perspective top view of the transillumination device showing the battery compartment of the device.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

As will be appreciated based upon the following disclosure, the transillumination device 1 of the present invention has a yellow-orange first light source 12 composed of LEDs having a wavelength in the range of 585-595 nm (preferably 590 nm), an amber second light source 14 composed of LEDs having a wavelength of light in the range of 600-610 nm (preferably 605 nm), and a lime green third light source 16 composed of LEDs having a wavelength of 535-545 nm (preferably 540 nm). Yellow-orange light has been found to be beneficial for transillumination of superficial veins, amber light has been found to be beneficial for transillumination of deeper veins and lime green light has been found to be beneficial for transillumination of arteries.

In addition, the transillumination device 1 has a unique shape and portable configuration that contains an on/off switch (or switching mechanism) 22 that allows the user to easily switch the transillumination device 1 on and off and a light control switch 24 to switch between the yellow-orange first light source 12, the amber second light source 14, and the lime green third light source 16 by simply pressing a button. In addition, the transillumination device 1 has a battery compartment 37 that houses a battery 34 to facilitate its portable usage. One single portable transillumination device 1 in accordance with the present invention contains all three LED light sources 12, 14, 16, each projecting light of a different color and wavelength which may be used for different purposes.

The transillumination device 1 as depicted in FIGS. 1, 2, 3 and 4 has a cylindrical shaped housing 10 with a first end 30 and a second end 32. The housing 10 is structured to be portable and small for ease of use in tiny neonates. The housing 10 is elongated as it extends from the first end 30 to the second end 32, and is substantially circular when viewed along a cross section taken perpendicular to the longitudinal axis extending between the first end 30 and the second end 32 of the housing 10. Although the housing 10 is substantially cylindrical, a portion of the housing 10 is flat so as to define a top surface 50 of the housing 10 (and of the transillumination device 1). The top surface 50 extends between the first end 30 and the second end 32 of the housing 10, and therefore includes a top surface first end 52 and a top surface second end 53 that correspond with the first end 30 and the second end 32, respectively, of the housing 10. Similarly, another portion of the housing 10 is flat so as to define a bottom surface 60 of the housing 10 (and of the transillumination device 1). The bottom surface 60 extends between the first end 30 and the second end 32 of the housing 10, and therefore includes a bottom surface first end and a bottom surface second end that correspond with the first end 30 and the second end 32, respectively, of the housing 10. While the housing 10, and ultimately the transillumination device 1, is described in accordance with a preferred embodiment as being substantially cylinder shaped, it is appreciated that it may take a variety of shapes as the preferences of different users might dictate.

Figure 4:
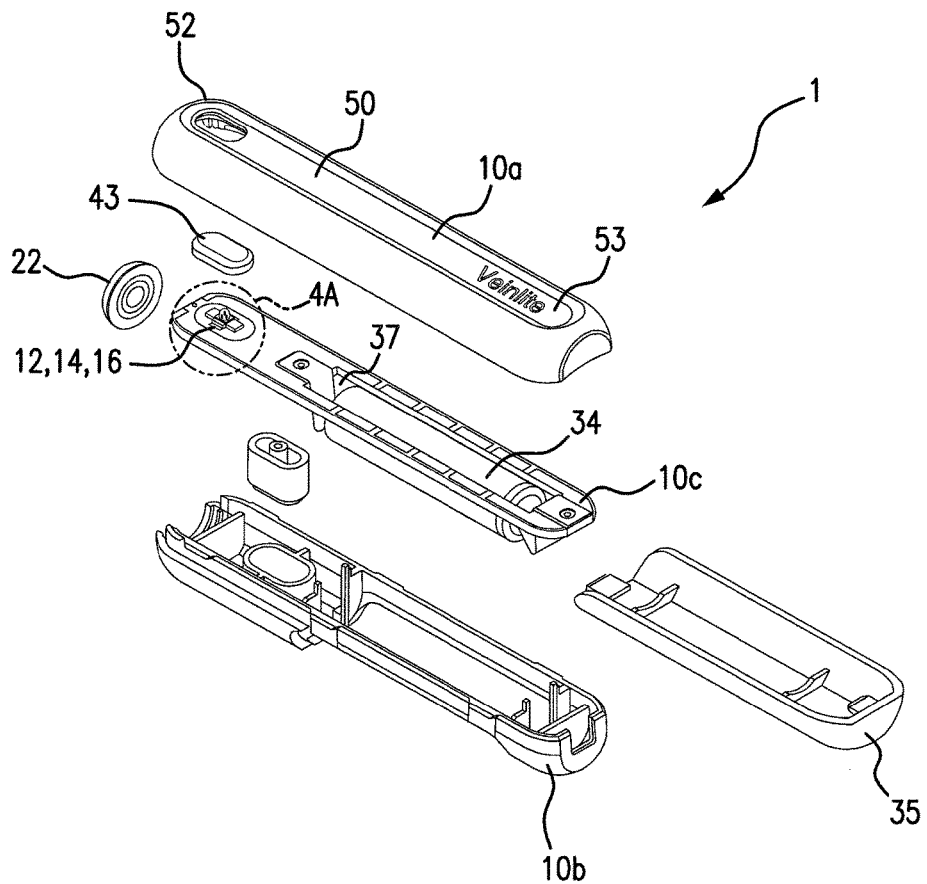
FIG. 4 is an exploded perspective view of the transillumination device showing the interior compartments of the transillumination device.

As shown with reference to FIG. 4, the housing 10 includes an upper housing member 10*a* and a lower housing member 10*b*, between which is supported a support member 10*c*. Various components (for example, the power source 34, the light sources 12, 14, 16, and the electronic circuitry (not shown)) of the transillumination device are supported by the support member 10*c*.

A transillumination light generating assembly 40 (that is, the assembly from which transilluminating light is projected in a manner discussed below in greater detail) is primarily located adjacent the top surface first end 52 of the top surface 50 of the housing 10. The transillumination light generating assembly 40 includes first, second and third light sources 12, 14, 16 that are used to create the transilluminating light projected by the transillumination light generating assembly 40.

The transillumination light generating assembly 40 includes a power source 34 for the first, second and third light sources 12, 14, and 16. In accordance with a preferred embodiment, the power source 34 is battery contained within the battery compartment 37 of the cylindrical shaped housing 10. Considering the need for replacing the battery, the housing 10 is provided with a cover member 35 that may be selectively removed for accessing the battery for replacement thereof.

The power source 34 is associated with a user controlled on/off switch 22 used to turn the transillumination device 1 on and off. A user controlled light control switch 24 is provided for actuation of the three light sources 12, 14, 16 in a controlled manner for the selective examination of a user's shallow veins, deeper veins or arteries. The user controlled on/off switch 22 is positioned at the first end 30 of the housing 10 can also be adapted to switch color, while the user controlled designated light control switch 24 is positioned along the exterior surface of the housing 10 to allow for ready access by users of the present transillumination device 1. The ability to switch colors from one switch is designed for maximum ease when working on neonates. In accordance with a preferred embodiment, the user controlled light control switch 24 is located on the bottom surface 60 of the housing 10 enabling a user to switch between the projection of yellow-orange light, amber light, and lime green light for the desired illumination.

The transillumination light generating assembly 40 further includes a substantially circular or oval shaped projection area 41 from which the light generated by the first, second and third light sources 12, 14, 16 is projected. As such, and in accordance with a preferred embodiment, the transillumination light generating assembly 40 includes a transparent glass or plastic lens 43 secured along the top section 50 of the housing 10 at the top surface first end 52, which defines the projection area 41. The transparent glass or plastic lens 43 is selected so as to allow for the complete passage of the light generated by the first, second and third light sources 12, 14, 16 therethrough for projection onto the skin of a patient being studied.

The projection area 41 of the transillumination light generating assembly 40 may be thought of as including a front end 41*a* positioned facing the first end 30 of the housing 10 and a distal end 41*b* facing the second end 32 of the housing 10. As mentioned above, the circular or oval shaped projection area 41 of transillumination light generating assembly 40 is positioned such that it rests in the same plane as the top surface 50 of the housing 10. The circular or oval shaped projection area 41 of transillumination light generating assembly 40 extends from the front edge of the housing 10 at the first end 30 thereof in a direction rearward so as to form a viewing area. The first, second and third light sources 12, 14, 16 are aligned with the circular or oval shaped projection area 41 of transillumination light generating assembly 40 so as to project light therefrom in a manner necessary to achieve transillumination in accordance with the present invention.

As briefly discussed above, the transillumination light generating assembly 40 includes first, second, and third light sources 12, 14, 16, of various desired frequencies, projecting light from the top surface 50 of the housing 10 for transillumination of shallow or deep veins and/or arteries, as desired, in accordance with the present invention. The first, second, and third light sources 12, 14, 16 are housed within the housing 10 in the area of the projection area 41 and are oriented so as to direct light through the transparent glass of plastic lens 43 formed in the top surface 50 of the housing 10. The first, second, and third light sources 12, 14, 16 are shaped and dimensioned to maximize illumination. In accordance with a preferred embodiment, each of the first, second, and third light sources 12, 14, 16 are oval or circular shaped. The first, second, and third light sources 12, 14, 16 are focused to project light of predetermined frequencies toward the user.

Each of the first, second, and third light sources 12, 14, 16 is composed of distinct LEDs used to creating different light colors as needed by the medical practitioner using the present transillumination device 1. The first light source 12 is composed of a plurality of LEDs generating yellow-orange light, the second light source 14 is composed of a plurality of LEDs generating amber light, and the third light source 16 is composed of a plurality of LEDs generating lime green light. The LEDs are 12, 14, 16 are all contained within the device and the light shines through lens 43. This combination of light sources enables both vein and artery transillumination. In accordance with a preferred embodiment, the yellow-orange LEDs of the first light source 12 produce light having a wavelength between 585-595 nm, preferably 590 nm. It is appreciated, the use of a yellow-orange light with the desired wavelength allows for enhanced imaging of superficial veins. In accordance with a preferred embodiment, the amber LEDs of the second light source 14 produce light have an approximate wavelength ranging from 600-610 nm, preferably 605 nm, for optimizing viewing of deeper veins. In accordance with a preferred embodiment, the lime green LEDs of the third light source 16 produces light having a wavelength ranging from 535-545 nm, preferably 540 nm, optimizes viewing of arteries. As a result, the transillumination device 10 has first, second, and third light sources 12, 14, 16 which can transmit yellow-orange, amber, and lime green LED light enabling transillumination of veins of different depths, and arteries, as desired. Further, yellow-orange LED light has higher absorption in venous blood than amber LED light and penetrates deeper in darker, pigmented skin; thus allowing better vein transillumination in dark skinned patients. Lime green LED light is optimal for artery viewing.

Figure 4A:
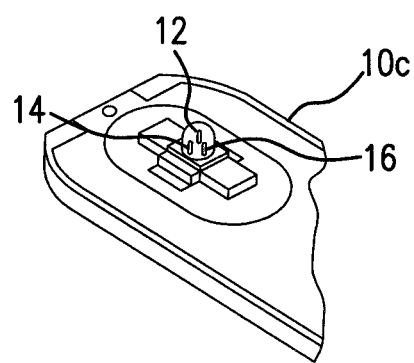
FIG. 4A is a detailed view of the section "4A" in FIG. 4.

As mentioned above, the first, second, and third light sources 12, 14, 16 are each composed of a plurality of LEDs. As shown with reference to FIG. 4A, the LEDs making up the respective first, second, and third light sources 12, 14, 16 are positioned along the substantially circular or oval shaped projection area 41 of the transillumination light generating assembly 40 so as to project light from the top surface 50 of the housing 10 toward a patient being examined.

In practice, the transillumination device 1 is placed near the patient's skin for vein or skin surface imaging, as desired. Other applications of transillumination devices are well known. In use, and the transillumination device 1 has been turned on, when the light control switch 24 is first depressed the first light source 12 is illuminated projecting either yellow-orange light from the series of LEDs for transillumination of veins. When the user controlled light control switch 24 is pressed again, the second light source 14 is illuminated projecting amber light from the series of LEDs for transillumination of deeper veins. When the user controlled light control switch 24 is pressed once again, the third light source 14 is illuminated projecting lime green light from the series of LEDs for transillumination of arteries. Finally, a combination of LEDs can also be selected for use at the same time. The top surface 50 of the housing 10 of the transillumination device 1 is preferably positioned about 2 inches to 6 inches away from the skin allowing the selected LED light to illuminate the vein or artery of a patient for examination. In this way, the transillumination device 1 enables the user to view the surface of an artery or vein using a single portable device. The ability to have one device to view arteries and shallow and deep veins provides significant savings to the user, by enabling such to occur in one simple handheld device.

Further, there is provided a method of viewing both arteries and shallow and deep veins of a patient by using one compact device. The method includes the steps of using the device as described above to perform an examination without the examiner having to use a separate device and interrupt the examination. Further still, examination is done via through the body transillumination, and side-transillumination is not required. Never before has a device capable of imaging arterial and venous blood vessels been provided.

Although the disclosed embodiment is manually controlled, it is contemplated an automatic sensor can be utilized such that when the unit is in touch with the skin, it will switch on the first light source and when it is away from the skin, it will turn on the second light source.

While the invention has been described with reference to a preferred embodiment, variations and modifications would be apparent to one of ordinary skill in the art. Such variations and modifications are encompassed by the invention.

I claim:

1. A transillumination device comprising in combination:
    a housing having a first end, a second end, a top surface, and a bottom surface,
    a yellow-orange first light source, an amber second light source, and a lime green third light source, the first light source being composed of LEDs producing light having a wavelength in the range of from 585-595 nm for illumination of shallow veins, the second light source being composed of LEDs producing light having a wavelength in the range of approximately 600-610 nm for transillumination of deeper veins, and the third light source being composed of LEDs producing light having a wavelength in the range of approximately 535-545 nm for illumination of arteries,
    an on/off switch for turning the transillumination device on and off,
    a light control switch for switching between the first, second, and third light sources, and
    a power source contained within the housing for powering the first, second, and third light sources.
2. The transillumination device as claimed in claim 1, further including a power compartment containing a battery for powering the first, second, and third light sources.

* * * * *